United States Patent
Johnson

(10) Patent No.: US 11,110,265 B2
(45) Date of Patent: Sep. 7, 2021

(54) UPDATING A VAD SYSTEM WITHOUT STOPPING THE PUMP

(71) Applicant: HeartWare, Inc., Miami Lakes, FL (US)

(72) Inventor: Thomas R. Johnson, Franklin, MA (US)

(73) Assignee: HeartWare, Inc., Miami Lakes, FL (US)

( * ) Notice: Subject to any disclaimer, the term of this patent is extended or adjusted under 35 U.S.C. 154(b) by 230 days.

(21) Appl. No.: 15/803,373

(22) Filed: Nov. 3, 2017

(65) Prior Publication Data

US 2019/0134286 A1    May 9, 2019

(51) Int. Cl.
| | |
|---|---|
| *G16H 40/40* | (2018.01) |
| *A61M 60/50* | (2021.01) |
| *A61M 60/148* | (2021.01) |
| *A61M 60/871* | (2021.01) |

(52) U.S. Cl.
CPC .......... *A61M 60/50* (2021.01); *A61M 60/148* (2021.01); *A61M 60/871* (2021.01); *G16H 40/40* (2018.01); *A61M 2205/50* (2013.01)

(58) Field of Classification Search
CPC ................ A61M 1/1086; A61M 1/122; A61M 2205/50; G16H 40/40
See application file for complete search history.

(56) References Cited

U.S. PATENT DOCUMENTS

| | | | |
|---|---|---|---|
| 6,688,861 | B2 | 2/2004 | Wampler |
| 7,575,423 | B2 | 8/2009 | Wampler |
| 7,976,271 | B2 | 7/2011 | LaRose et al. |
| 8,419,609 | B2 | 4/2013 | Shambaugh, Jr. et al. |
| 9,744,280 | B2 | 8/2017 | Schade et al. |
| 2011/0160516 | A1* | 6/2011 | Dague ................. A61M 1/1086 600/16 |
| 2012/0172657 | A1* | 7/2012 | Marseille ............ A61M 1/1086 600/16 |
| 2015/0290376 | A1 | 10/2015 | Schade et al. |
| 2015/0290378 | A1 | 10/2015 | Schade et al. |
| 2016/0095968 | A1* | 4/2016 | Rudser ................ A61M 1/1086 600/17 |

FOREIGN PATENT DOCUMENTS

| | | |
|---|---|---|
| WO | 2007090050 A2 | 8/2007 |
| WO | 2011035308 A1 | 3/2011 |
| WO | 2017087380 A1 | 5/2017 |

OTHER PUBLICATIONS

International Search Report and Written Opinion dated Jan. 22, 2019, for corresponding International Application No. PCT/US2018/057653; International Filing Date: Oct. 26, 2018 consisting of 10-pages.

* cited by examiner

*Primary Examiner* — Joseph M Dietrich
(74) *Attorney, Agent, or Firm* — Christopher & Weisberg, P.A.

(57) ABSTRACT

A remote controller updating system for an implantable blood pump including an implantable blood pump, an implantable controller coupled to the implantable blood pump, and a pump driveline including a data network connection in communication with the implantable controller. The system may also include a pump connector coupled to the pump driveline, a remote controller couplable to the implantable blood pump, and a system update assembly including a system update connector couplable to the pump connector and a power source coupled to the system update connector.

11 Claims, 3 Drawing Sheets

UPDATING A VAD SYSTEM WITHOUT STOPPING THE PUMP

STATEMENT REGARDING FEDERALLY SPONSORED RESEARCH OR DEVELOPMENT n/a

TECHNICAL FIELD

The present invention relates to implantable blood pumps, and, more particularly, to a method and system for updating a remote controller of an implantable blood pump, while maintaining the blood pump in continuous operation.

BACKGROUND

Implantable blood pumps provide mechanical circulatory support to patients having a weakened or otherwise compromised heart. Generally, an implantable blood pump, such as a ventricular assist device ("VAD"), includes a pumping mechanism to move blood from the heart to the rest of the body. For example, in operation, the blood pump draws blood from a source, such as the patient's heart and impels the blood into an artery, such as the patient's ascending aorta or peripheral artery.

Known implantable blood pumps are typically operated by a controller located remote to the patient. A cable, such as a transcutaneous electrical cable, connects the controller to the implanted blood pump. The controller includes electronics, such as hardware and software, which store various levels of information, such as information associated with the control and operation of the blood pump, patient parameters, and the like. The electronics may be updated through software updates, controller exchanges, and the like. Unfortunately, known systems and methods of updating the electronics often require the blood pump to be stopped, which stops blood flow and is therefore hazardous or fatal to the patient.

SUMMARY

The present invention advantageously provides a remote controller updating system for an implantable blood pump. The system may include an implantable blood pump, an implantable controller coupled to the implantable blood pump, and a pump driveline including a data network connection in communication with the implantable controller. The system may also include a pump connector coupled to the pump driveline, a remote controller couplable to the implantable blood pump, and a system update assembly including a system update connector couplable to the pump connector and a power source coupled to the system update connector.

In one aspect of this embodiment, the implantable blood pump includes an operative mode and the remote controller includes an update mode, the update mode being actuatable when the system update assembly is coupled to the pump connector.

In one aspect of this embodiment, the update mode includes one of a group consisting of a system installation and a remote controller exchange configuration.

In one aspect of this embodiment, the implantable controller includes a processor configured to control an operation of the implantable blood pump.

In one aspect of this embodiment, the system may include a second remote controller exchangeable with the remote controller, the remote controller and the second remote controller each including a remote power source being coupled thereto.

In one aspect of this embodiment, the data network connection includes a bi-directional communication pathway between the implantable controller and the remote controller.

In one aspect of this embodiment, the system may include a controller connector couplable to the pump connector.

In one aspect of this embodiment, the system may include a controller driveline having a proximal portion and a distal portion opposite the proximal portion, the distal portion being coupled to the remote controller and the proximal portion being coupled to the controller connector.

In one aspect of this embodiment, the pump connector may include a first receiving portion and a second receiving portion, the first receiving portion sized to receive the controller connector and the second receiving portion sized to receive the system update In one aspect of this embodiment, the pump connector and the system update connector are coupled to each other using a magnetic force.

In one aspect of this embodiment, the implantable blood pump includes a motor and the implantable controller is configured to control the motor.

In another embodiment, a method of updating a remote controller of an implantable blood pump includes coupling a pump driveline to an implantable blood pump having an implantable controller, the pump driveline including a pump connector being coupled thereto, coupling a remote controller to the implantable blood pump, and coupling a system update connector to the pump connector, the system update connector including and a power source coupled thereto. The method may also include translating the remote controller to an offline mode and updating the remote controller in the offline mode, the update including at least one of a group consisting of a remote controller exchange and a remote controller In one aspect of this embodiment, the method may include programming the implantable controller to perform a motor control function.

In one aspect of this embodiment, the method may include maintaining the implantable blood pump in an operative mode during the updating of the remote controller.

In one aspect of this embodiment, the method may include coupling a controller connector having a controller driveline to the pump connector.

In one aspect of this embodiment, the method may include coupling the controller connector to a first receiving portion of the pump connector and coupling the system update connector to a second receiving portion of the pump connector, the system update connector and the pump connector being coupled to each other using a magnetic force.

In one aspect of this embodiment, the pump driveline may include a data network connection having a bi-directional communication pathway between the implantable controller and the remote controller.

In one aspect of this embodiment, the method may include translating the remote controller to an online mode and disconnecting the system update connector from the pump connector.

In one aspect of this embodiment, the method may include continuously providing a power source to the blood pump during the updating of the remote controller.

In another embodiment, a remote controller updating system for an implantable blood pump includes an implantable blood pump including a housing having a motor therein and an implantable controller disposed within the housing for controlling the motor. The system may also include a pump driveline coupled to the implantable blood pump, the pump driveline including a data network connection in communication with the implantable controller, a pump connector coupled to the pump driveline, a remote controller couplable to the implantable blood pump, and a system update assembly including a system update connector couplable to the pump connector and a power source coupled to the system update connector.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
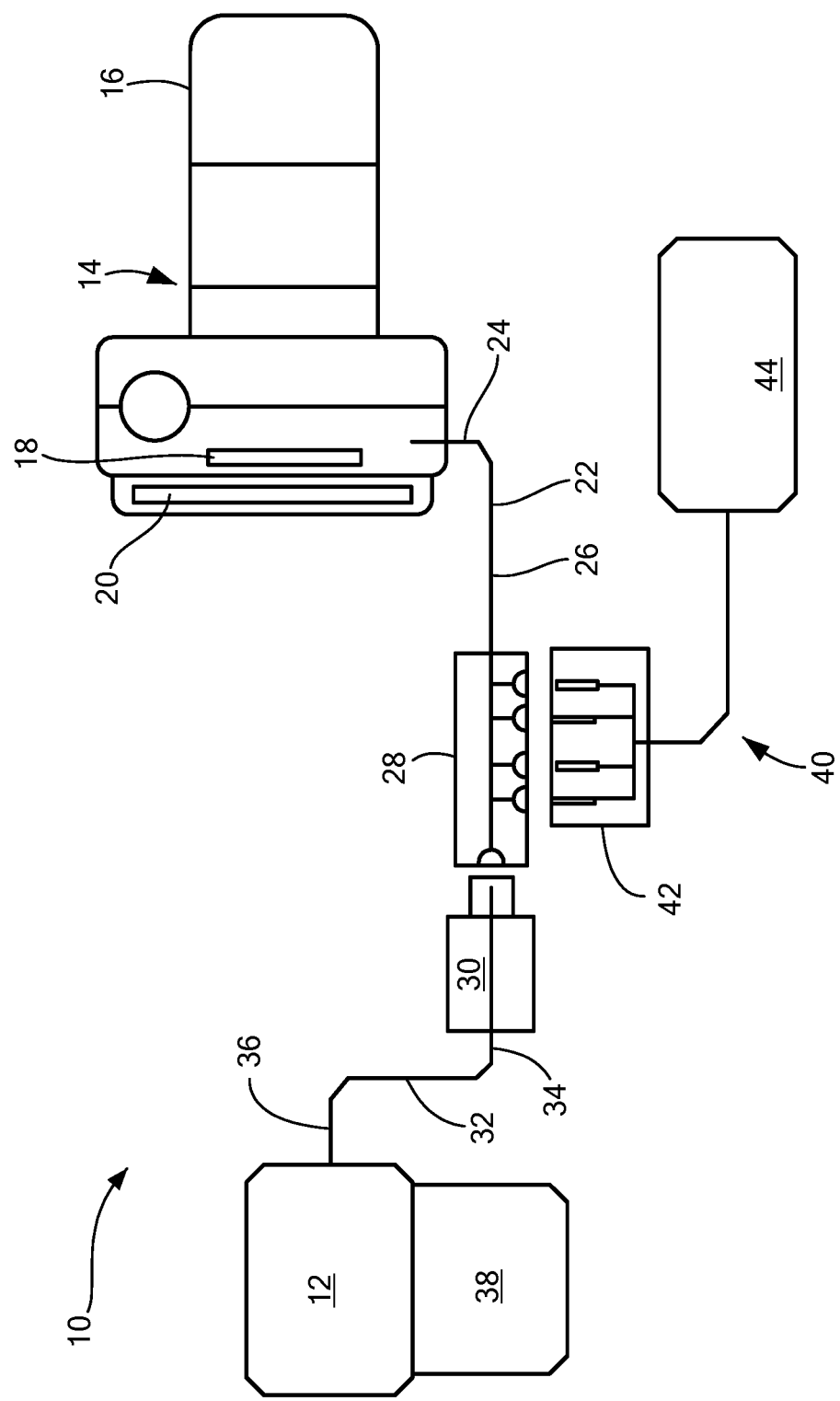
FIG. 1 is a schematic view of a remote controller updating system for an implantable blood pump.

Referring now to the drawings in which like reference designators refer to like elements there is shown in FIG. 1 a remote controller updating system constructed in accordance with the principles of the present application and designated generally "10." The system 10 may be configured to update a remote controller 12 of an implantable blood pump 14 when the blood pump 14 is implanted within a patient, without stopping the blood pump 14. The remote controller 12 may include, but is not limited to, operational components, such as a control unit, a display, a user input interface, a processor, a memory, and a network interface. The term "update" is used herein in its broadest possible sense and includes controller exchanges and one or more updates and/or upgrades to the operational components.

The blood pump 14 may be of various types, including but not limited to, a ventricular assist device sold under the designation HVAD® by HeartWare, Inc. The blood pump 14 generally includes a housing 16 having one or more motors 18, and internal operating components, as is known in the art and described for example in U.S. Pat. Nos. 6,688,861; 7,575,423; 7,976,271; and 8,419,609, the disclosures of which are incorporated by reference herein. The housing 16 and the internal operating components may vary depending upon the type of blood pump 14 and the description provided herein is exemplary and not intended to be limiting.

The blood pump 14 may include an operative mode and an inoperative mode. In the operative mode, a power source is supplied to the motor 18 and thus the motor 18 is operating to pump the patient's blood. In the inoperative mode, the power source is not supplied to the motor 18 and therefore the motor is not operating. As a result, blood flow to the patient halts or ceases, which could be hazardous or fatal for the patient.

In one configuration, the system 10 may include an implantable controller 20 coupled to the blood pump 14. The implantable controller 20 may be integral with or removably coupled to the blood pump 14 and may be configured to control operation of the motor 18. For example, the implantable controller 20 may be disposed within the housing 16 and may include a control unit having one or more controllers, processors, and/or software modules containing instructions or algorithms to provide for the operation and/or performance of the power and/or operation of the blood pump 14. For example, the implantable controller 20 may be programmed to include a motor control function for controlling the motor 18.

The system 10 may include a pump driveline 22 having a data network connection in communication with the implantable controller 20 and configured to extend outside of the patient. For example, the pump driveline 22 may include a distal portion 24 and a proximal portion 26 opposite the distal portion 24. The distal portion 24 may include a pump connector 28 configured to couple to a controller connector 30. The proximal portion 26 may be coupled to the housing 16.

Referring still to FIG. 1, a controller driveline 32 is shown having a distal portion 34 extending from the controller connector 30 and an opposing proximal portion 36 coupled to a remote controller 12, which may be located external to the patient. The remote controller 12 may include one or more remote power sources 38, such as a battery and or an AC/DC port, for supplying power to the blood pump 14 when the pump connector 28 is coupled to the controller connector 30. The pump connector 28 and the controller connector 30 may provide for an efficient connection and disconnection between the remote controller 12 and the blood pump 14.

The remote controller 12 may include a control unit having one or more controllers, processors, and/or software modules containing instructions or algorithms to provide for performing various functions associated with the blood pump 14, such as collecting pump and/or patient related information from the blood pump, providing updates to the implantable controller 20, transmitting power to the blood pump 14, and the like. The data network connection of the pump driveline 22 may include a bi-directional communication pathway between the implantable controller 20 and the remote controller 12 to provide the exchange of information therebetween.

Figure 2:
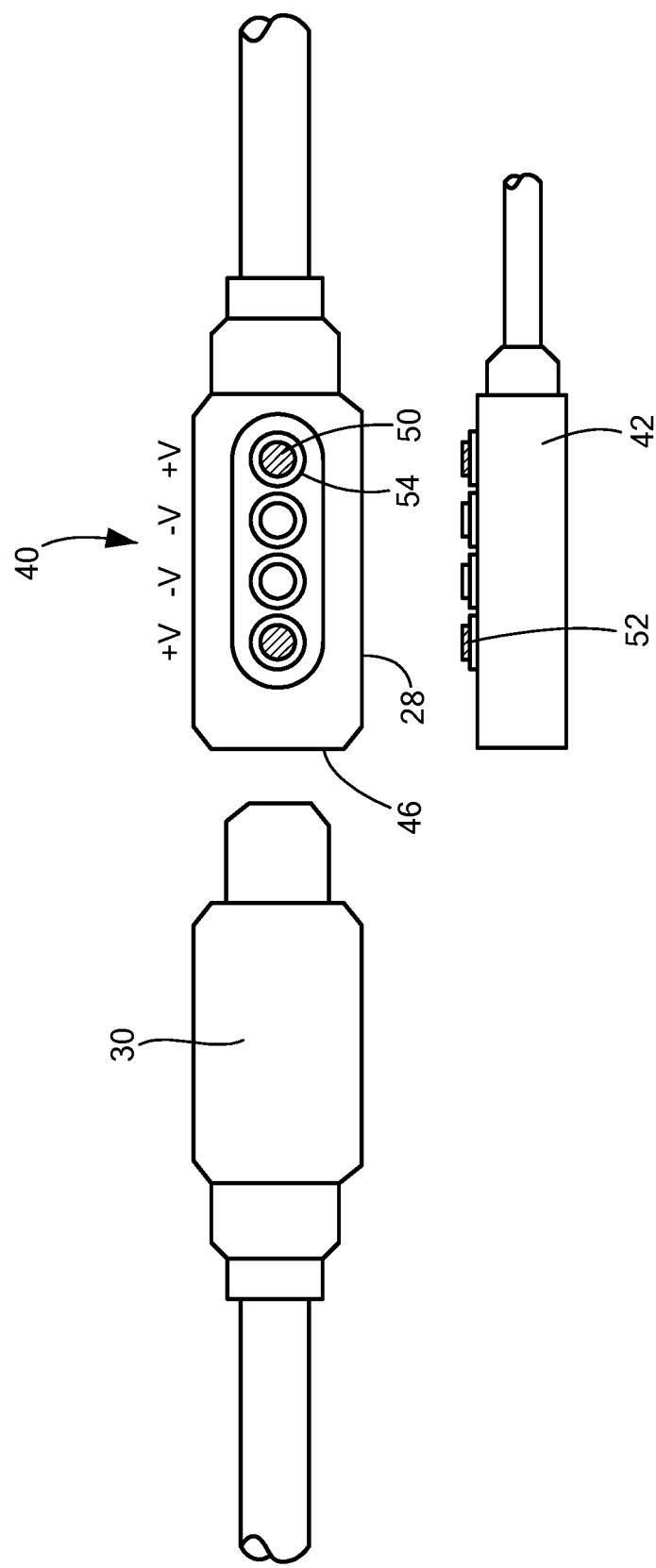
FIG. 2 is a front view of a pump connector, a side view of a controller connector, and a side view of a system update connector of the system of FIG. 1.

With reference to FIGS. 1 and 2, the system 10 may include a system update assembly 40 having a system update connector 42 including a power source 44 (FIG. 1), such as a battery and/or an AC/DC adapter coupled to the system update connector 42. The system update assembly 40 may be coupled to the pump connector 28 to perform the remote controller 12 update, while keeping the blood pump 14 in the operative mode, as explained in further detail herein.

With reference to FIG. 2, the pump connector 28 may include a first receiving portion 46 sized to receive the controller connector 30 and a second receiving portion 48 sized to receive the system update connector 42. The first receiving portion 46 may be in the form of an aperture (not shown) for receiving the pump connector 28 within the aperture. In the alternative, the first receiving portion 46 may include a fastener or another type of coupling mechanism.

In one configuration, the second receiving portion 48 may include four electrical contacts 50 for receiving four electrical contacts 52 exposed on the system update connector 42 to transmit power through the system update connector 42 to the blood pump 14. Although FIG. 2 shows four electrical contacts 50, 52, more or less electrical contacts 50, 52 may be used. In addition to the electrical contacts 50, the system update connector 42 may include one or more magnets, such as one or more magnetic polymers 54 surrounding the electrical contacts 52. As such, the pump connector 28 and the system update connector 42 may be coupled to each other using a magnetic force that allows for a relatively simple and efficient connection and disconnection. In the alternative, the second receiving portion 48 may be coupled to the pump connector 28 using a fastener or another type of coupling mechanism.

Figure 3:
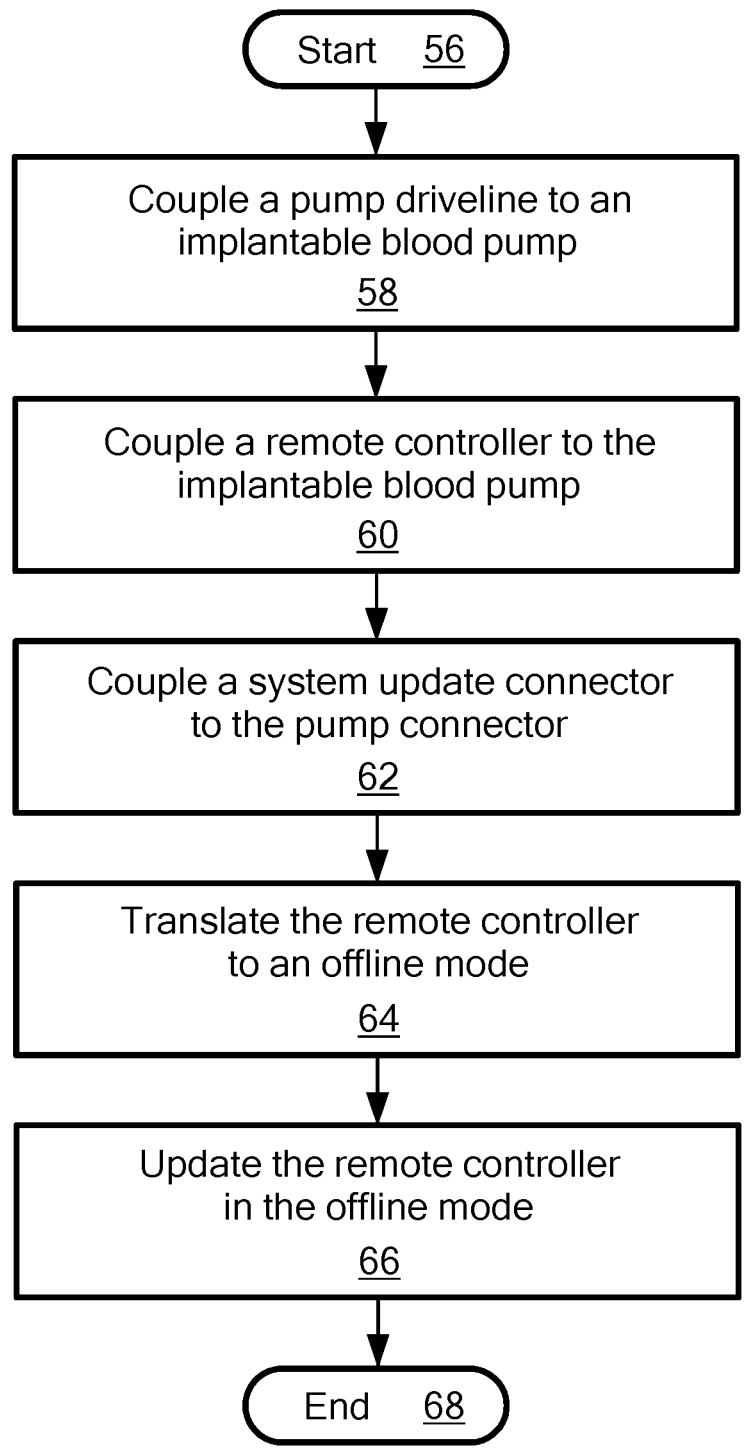
FIG. 3 is a flow chart illustrating a method of updating a remote controller for the implantable blood pump of FIG. 1.

With reference to FIG. 3, the remote controller 12 may benefit from one or more updates. FIG. 3 shows one configuration of a series of steps associated with a method of updating the remote controller 12. The steps shown in FIG. 3 are exemplary and more or less steps may be included and the order of the steps may vary.

In one configuration, the method begins with step 56 and proceeds to step 58 in which the pump driveline 22 is coupled to the blood pump 14. The pump driveline 22 may be coupled to the blood pump 14 using one or more methods known in the art. In step 60, the remote controller 12 is coupled to the blood pump 14, such as through connecting the pump connector 28 to the controller connector 30.

In step 62, the system update connector 42 may be coupled to the pump connector 28, such as through the use of the magnetic force. The system update connector 42 includes the system update power source 44 coupled thereto with power being supplied to the blood pump 14. When power is supplied to the blood pump 14 through the system update power source 44, in step 64, the remote controller 12 may be translated to an update mode. In one configuration, the update mode includes the remote controller 12 being switched from an online mode, in which the remote controller 12 is in communication with the implantable controller 20 through the data network, to an offline mode. The transition from the online mode to the offline mode may occur through a switch, button, voice command, or the like, on the remote controller 12. In the offline mode, communication between the remote controller 12 and the implantable controller 20 is disrupted as the remote controller 12 is offline.

In step 66, the method includes updating the remote controller 12. The update may include system installations for updating or upgrading the remote controller 12, while keeping the remote controller 12 coupled to the blood pump 14. In the alternative, the update may include a remote controller exchange configuration in which the remote controller 12 is exchanged for a second remote controller 12. The second remote controller 12 may be configured to operate in a similar manner to the initial remote controller 12 but may include system updates, system upgrades, and the like.

In order to promote patient safety, because the implantable controller 20 is configured to control operation of the motor 18, and the system update power source 44 is configured to supply power to the blood pump in the absence of the remote controller 12, the blood pump 14 may continue to operate when the remote controller 12 is updated. In other words, power is continuously provided to the blood pump 14 by the system update power source 44 during the update, thus the blood flow from the blood pump 14 remains unaffected by a remote controller 12 update. When the update is completed, the remote controller 12 may be translated from the offline mode to an online mode. In the online mode, power is provided to the blood pump 14 through the remote controller 12 and the remote power source 38, thus the system update connector 42 may be disconnected from the pump connector 28. The method ends at step 68.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A remote controller updating system for an implantable blood pump comprising:
    an implantable blood pump;
    an implantable controller coupled to the implantable blood pump;
    a pump driveline including a data network connection in communication with the implantable controller;
    a pump connector coupled to and extending along a portion of the pump driveline;
    a remote controller couplable to the pump connector, the data network connection of the pump driveline having a bi-directional communication pathway between the implantable controller and the remote controller; and
    a system update assembly including a system update connector couplable to the pump connector and a power source coupled to the system update connector, the power source being configured to supply power to the implantable blood pump when the remote controller is in an update mode.

2. The system of claim 1, wherein the implantable blood pump includes an operative mode and the remote controller includes the update mode, the update mode being actuatable when the system update assembly is coupled to the pump connector.

3. The system of claim 2, wherein the update mode includes one of a group consisting of a system installation and a remote controller exchange configuration.

4. The system of claim 1, wherein the implantable controller includes a processor configured to control an operation of the implantable blood pump.

5. The system of claim 4, further comprising a second remote controller exchangeable with the remote controller, the remote controller and the second remote controller each including a remote power source being coupled thereto.

6. The system of claim 1, further comprising a controller connector couplable to the pump connector.

7. The system of claim 6, further comprising a controller driveline having a proximal portion and a distal portion opposite the proximal portion, the distal portion being coupled to the remote controller and the proximal portion being coupled to the controller connector.

8. The system of claim 6, wherein the pump connector includes a first receiving portion and a second receiving portion, the first receiving portion sized to receive the controller connector and the second receiving portion sized to receive the system update connector.

9. The system of claim 6, wherein the pump connector and the system update connector are coupled to each other using a magnetic force.

10. The system of claim 1, wherein the implantable blood pump includes a motor and the implantable controller is configured to control the motor.

11. A remote controller updating system for an implantable blood pump comprising:
    an implantable blood pump including a housing having a motor therein;
    an implantable controller disposed within the housing for controlling the motor;

a pump driveline coupled to the implantable blood pump, the pump driveline including a data network connection in communication with the implantable controller;
a pump connector coupled to and extending a long a portion of the pump driveline;
a remote controller couplable to the pump connector, the data network connection of the pump driveline having a bi-directional communication pathway between the implantable controller and the remote controller; and
a system update assembly including a system update connector directly couplable to the pump connector and a power source coupled to the system update connector, the power source being configured to supply power to the implantable blood pump when the remote controller is in an update mode.

* * * * *